United States Patent [19]

Cookson et al.

[11] Patent Number: 5,180,830
[45] Date of Patent: Jan. 19, 1993

[54] PROCESS FOR PREPARING HINDERED AMINE LIGHT STABILIZERS

[75] Inventors: Gleason O. Cookson, Taunton, Mass.; Vu A. Dang, Bear; Krishna Raman, Wilmington, both of Del.

[73] Assignee: Himont Incorporated, Wilmington, Del.

[21] Appl. No.: 690,760

[22] Filed: Apr. 24, 1991

[51] Int. Cl.$^5$ ............................................. C01D 401/12
[52] U.S. Cl. ...................................... 546/222; 546/242
[58] Field of Search ................................. 546/222, 242

[56] References Cited

U.S. PATENT DOCUMENTS 4,021,432  5/1977  Holt et al. ............................ 546/188
4,461,898  7/1984  Meier et al. ......................... 546/188

Primary Examiner—Marianne M. Cintins
Assistant Examiner—Catherine S. Kilby Scalzo

[57] ABSTRACT

Disclosed is a process for the preparation of hindered amine light stabilizers by reacting (a) an alkyl substituted-4-hydroxypiperidine with (b) a dicarboxylic acid ester, in the presence of a catalyst system comprising a basic inorganic compound and a polar aprotic organic compound.

17 Claims, No Drawings

PROCESS FOR PREPARING HINDERED AMINE LIGHT STABILIZERS

FIELD OF THE INVENTION

This invention relates to a process for the preparation of diesters of an alkyl substituted-4-hydroxypiperidine compound from certain organic esters. More particularly this invention relates to a process for preparing diesters of an alkyl substituted-4-hydroxypiperidine compound from dicarboxylic acid esters using a catalyst system comprising a basic inorganic compound and a polar aprotic organic compound.

BACKGROUND OF THE INVENTION

Hindered amine light stabilizers (HALS) based on diesters of bis(substituted-piperidine) are known and are prepared by various methods. One method of preparation is transesterification of a dicarboxylic acid ester by reacting a dicarboxylic acid ester, such as dimethylsebacate, with a substituted-4-hydroxypiperidine in the presence of a catalyst, such as an alkali metal amide, in the absence or presence of an inert solvent, such as toluene, to form the diester of the piperidine alcohol employed and methanol as the by-product.

For example, U.S. Pat. No. 4,021,432 describes the transesterification of dicarboxylic acid esters in the absence or presence of an inert solvent, such as benzene, toluene or xylene, with a substituted piperidinol compound in the presence of a transesterification catalyst, an alkali metal amide such as lithium amide, whereby the alcohol produced in the reaction is removed. However, the total reaction time is from about 4 to about 7 hours.

In U.S. Pat. No. 4,461,898 mixtures of esters of polyalkylpiperidine derivatives are prepared by reacting 2 mols of a Piperidinol with 0.9 to 1.3 mols of a diester, in the melt, at between 100° and 145° C., in the presence of an alkali metal amide, preferably lithium amide, as a catalyst. After the reaction has started, the alcohol formed is removed by distillation, first at atmospheric pressure, and then under vacuum for an additional 2 to 3 hours.

SUMMARY OF THE INVENTION

It has now been found that by carrying out the transesterification of a diester with an alcohol in the presence of a catalyst system containing a polar aprotic solvent, in addition to the basic inorganic compound, Provides higher conversion yields of the desired diester in shorter reaction times.

Accordingly, the present invention provides a process for preparing hindered amine light stabilizers by reacting (a) an alkyl substituted-4-hydroxypiperidine having the following general formula:

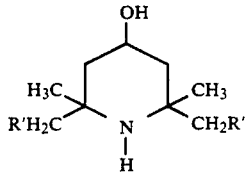

where R' is hydrogen or methyl, with (b) a dicarboxylic acid ester having the following general formula:

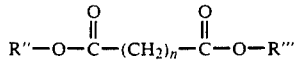

where R'' and R''' are a $C_1$-$C_{12}$ linear or branched alkyl, a $C_5$-$C_{12}$ cycloalkyl, a $C_6$-$C_{12}$ aryl, or a $C_7$-$C_{12}$ alkaryl or aralkyl and may be the same or different, and n is a number from 1-12, in the presence of a basic inorganic compound/polar aprotic organic compound catalyst system, at a temperature from 80° to 165° C. and under vacuum or under a flow of an inert gas at atmospheric pressure, wherein the alkyl substituted-4-hydroxypiperidine is present in an amount of from 2 to 3.2 moles per mole of dicarboxylic acid ester.

DETAILED DESCRIPTION OF THE INVENTION

The preferred alkyl substituted 4-hydroxypiperidine compound useful in the practice of the present invention is 2,2,6,6-tetramethyl-4-hydroxypiperidine. The alkyl substituted-4-hydroxypiperidine is present in an amount of from 2 to 3.2 moles per mole of dicarboxylic acid ester used. Preferably, the alkyl substituted-4-hydroxypiperidine is present in an amount of from 2.2 to 3 moles per mole of dicarboxylic acid ester.

Suitable dicarboxylic acid esters useful in the present invention are those derived from malonic, succinic, glutaric, adipic, pimelic, suberic, azelaic, sebacic or 1,12-dodecanedoic acid. Preferred is the ester of sebacic, and most preferred is dimethylsebacate (DMS).

The basic inorganic compounds useful in the practice of this invention are alkali metal compounds, such as alkali metal hydride, alkali metal hydroxides, alkali metal alkoxides, alkali metal amides and alkali metal alkyl amides. Alkali metals for the basic compounds include lithium, sodium and potassium. Examples of the basic inorganic compounds useful in the present invention are lithium hydride, sodium hydride, lithium hydroxide, sodium hydroxide, potassium hydroxide, potassium methoxide, sodium methoxide, lithium methoxide, potassium ethoxide, sodium ethoxide, lithium ethoxide, potassium tert-butoxide, sodium tert-butoxide, n-butyllithium, phenyl potassium, phenyl sodium, lithium amide, potassium amide and lithium diisopropyl amide. Preferred is lithium amide. The basic inorganic compound is typically present in an amount from about 1 to 30 mole % per mole of dicarboxylic acid ester used. Preferably, the basic inorganic compound is present in an amount of from about 2 to 15 mole %, and most preferably, from 5 to 7 mole % per mole of dicarboxylic acid ester.

In order for a polar aprotic organic compound to be useful as a co-catalyst in the practice of this invention, it must have sufficient polarity to dissolve the particular ingredients employed at the reaction temperature used and it must be capable of complexation with the metal ion of the basic inorganic compound used. Such polar aprotic organic compounds include N-methylpyrrolidinone (NMP), 1,2-dimethoxybenzene (DMB), N,N-dimethylacetamide (DMAC), hexamethyltriphosphoramide, tetramethylenesulfone, tetraethylene glycol dimethyl ether, ethylene glycol dimethylether, dimethylaminopyridine (DMAP), N,N,N',N'-tetramethylethylenediamine (TMEDA) and 1,3-dimethyl-2-imidazolidinone (DMI). Dimethylsulfoxide (DMSO) and crown ethers, such as 12-crown-4, can also be used as the solvent and co-catalyst and are within the broadest aspects of the invention. However, crown ethers are toxic and may leave impurities in the final products making them unacceptable for use in the manufacture of plastic articles to be used in contact with food, medicines, pharmaceuticals and other materials which are eaten, taken orally or intravenously or topically applied. NMP, DMI, DMB and DMAC are preferred, with DMB being the most preferred. The co-catalyst is present in an amount of from 5 to 20 wt. %, preferably 7 to 12 wt. %, based on the total reactants.

According to the process of this invention, an alkyl substituted-4-hydroxypiperidine of the formula described above, is reacted with a dicarboxylic acid ester of the formula described above, in the presence of a polar aprotic organic compound at a temperature of from 80°-110° C. The basic inorganic compound is added and the reaction mixture is heated to a temperature of from 145°-165° C. while continuously sparging with an inert gas, such as nitrogen, at atmospheric pressure or under vacuum. The inert gas or vacuum facilitates the removal of the by-product. Preferably the process is carried out under a flow of inert gas at atmospheric pressure.

As used in the present invention, the term "by-product" refers to the alkanol formed during the transesterification synthesis, and "side-product" refers to any product other than the desired product which may be formed during the transesterification synthesis.

The order of addition of the polar aprotic organic compound and the basic inorganic compound to the reaction medium containing the ester and alcohol is not critical, since the reaction between reactants does not start until all of the reactants are present. The basic inorganic compound can be introduced into the reaction medium before the polar aprotic organic compound. Preferably, the polar aprotic organic compound is added to the reaction mixture first, in order to decrease the viscosity of the reaction mixture.

When sparging with an inert gas, such as nitrogen, in the practice of this invention, the sparging is done at a flow rate of from 0.2 L/min. to 1 L/min., preferably from 0.5 to 1 L/min., most preferably at a low rate of about 0.5 L/min., at ambient pressure.

When the removal of the by-product is carried out under a vacuum, the pressure must be low enough to effectively remove the by-product. The pressure can be from 1 mmHg to 200 mmHg, preferably from 30 to 150 mmHg. Also, solvent refluxation plays an important role when the vacuum process is used, in that it aids in the removal of the by-product and accelerates the transesterification reaction.

Most preferably, the reaction mixture is rapidly agitated during the removal of the by-product to form homogeneous mixture thereby preventing the trapping of the by-product within the reaction medium which is somewhat viscous. The reaction is typically agitated from about 450 rpm to about 2000 rpm in a lab scale reaction. In a commercial scale process, typical commercial turbine mixers would be used to provide sufficiently rapid mixing.

Once the by-product has been removed, the reaction medium is then neutralized with an acid, such as glacial acetic acid, at a temperature of from 100°-110° C. After about 5-25 minutes, the reaction mass is crystallized from methanol and water to yield the final product.

The temperature range for carrying out the reaction of the present invention is from 80°-165° C., preferably from 100°-155° C.

The present invention is illustrated in greater detail by the examples of the invention set forth below.

All parts and percentages are by weight unless otherwise indicated.

The organic diester compounds were analyzed by gas chromatography using a Hewlett-Packard Model 5890 Gas Chromatograph and a Hewlett-Packard Model 3396A for integration and data handling. The column was a 6'×1/8" OD stainless steel column packed with 3% SE-54 on 80-100 mesh chromosorb, with a thermal conductivity detector. The column oven was programmed from 100° C. to 320° C. at 10° C./min. and held at the upper limit for 10 minutes. The composition was determined by area percent calculation.

EXAMPLE 1

To a reaction vessel equipped with a mechanical stirrer, a thermometer, a condenser maintained at 70° C, a trap and nitrogen sparge tube are added dimethylsebacate (25 g, 109 mmoles), 2,2,6,6-tetramethyl-4-hydroxypiperdine (34 g, 217 mmoles) and N-methylpyrrolidinone (7 ml) and heated to 100° C. Then lithium amide (0.124 g, 5.4 mmoles) is added with agitation and the reaction mixture is heated to 150°-155° C. for 3 hours at atmosphere pressure. During this period, nitrogen is continuously introduced subsurface at a rate of 0.5 L/min. to remove the generated methanol. The completed reaction mass is then cooled down to 100° C. and neutralized with glacial acetic acid. Analysis by gas chromatography indicated that 99% of bis(2,2,6,6-tetramethyl-4-piperidinyl)sebacate is obtained, based on the dimethylsebacate.

Control

To a reaction vessel equipped with a mechanical stirrer, a thermometer, a condenser maintained at 70° C. and a nitrogen sparge tube are added dimethylsebacate (23 g, 100 mmoles) and 2,2,6,6-tetramethyl-4-hydroxypiperidine (31.4 g, 200 mmoles) and heated to 100° C. Then lithium amide (0.124 g, 5 mmoles) is added with agitation and the reaction mixture is heated to 150° C. while nitrogen is continuously introduced subsurface (0.5 L/min.) to remove the generated methanol. Cleaning of the condenser was necessary from time to time due to the sublimation of the tetramethylhydroxypiperidine starting material on the condenser. After approximately 4.5 hours the reaction mixture was stopped and the reaction crude is cooled to 100° C. and neutralized with glacial acetic acid. Analysis by gas chromatography indicated that a mixture of 89% bis(2,2,6,6-tetramethyl-4-piperidinyl)sebacate and 11% of the half-ester, methyl(2,2,6,6-tetramethyl-4-piperidinyl)sebacate is obtained, based on the dimethylsebacate.

EXAMPLE 2

To a reaction vessel equipped with a mechanical stirrer, a thermometer, a condenser maintained at 70° C., a trap and nitrogen sparge tube are added dimethylsebacate (25 g, 109 mmoles), 2,2,6,6-tetramethyl-4-hydroxypiperidine (37.5 g, 239 mmoles) and N-methylpyrrolidinone (7 ml) and heated to 100° C. Then lithium amide (0.124 g, 5.4 mmoles) L 10 is added with agitation and the reaction mixture is heated to 150°-155° C. for 3 hours at atmospheric pressure. During this period, nitrogen is continuously introduced subsurface at a rate of 0.5 L/min. to remove the generated methanol. The completed reaction mass is then cooled down to 100° C. and neutralized with glacial acetic acid. Analysis by gas chromatography indicated that 99% of bis(2,2,6,6-tetramethyl-4-piperidinyl)sebacate is obtained, based on the dimethylsebacate.

EXAMPLE 3

The procedure and ingredients of Example 2 are used except that 7 ml of dimethoxybenzene is used instead of N-methylpyrrolidinone. After 3 hours, analysis by gas chromatography indicated that 99% of bis(2,2,6,6-tetramethyl-4-piperidinyl)sebacate is obtained, based on the dimethyl sebacate.

EXAMPLE 4

To a reaction vessel equipped with a mechanical stirrer, a thermometer, a condenser maintained at 70° C., a trap and a nitrogen sparge tube are added dimethylsebacate (14.0 g, 61 mmole), 2,2,6,6-tetramethyl-4-hydroxypiperidine (25 g, 158 mmole) and N-methylpyrrolidinone (5 ml) and heated to 100° C. Lithium amide (0.07 g, 3 mmole) was then added and the reaction was heated to 150°-155° C. for 3 hours. During this period, nitrogen is continuously introduced subsurface (0.5 L/min.) to remove the generated methanol. The reaction was stopped and the reaction crude was cooled to 100° C. and neutralized with gacial acetic acid. Analysis by gas chromatography indicated that 99% of bis(2,2,6,6-tetramethyl-4-piperidinyl)sebacate is obtained, based on the dimethylsebacate.

EXAMPLE 5

To a reaction vessel equipped with a mechanical stirrer, a thermometer, a condenser maintained at 70° C., a trap and a nitrogen inlet are added dimethylsebacate (11.5 g, 50 mmole), 2,2,6,6-tetramethyl-4-hydroxypiperidine (23.6 g, 150 mmole) and N-methylpyrrolidinone (4 g) and heated to 100° C. with stirring under a nitrogen blanket. Then lithium amide (0.020 g, 0.87 mmoles) was added to the reaction mixture. With agitation and under a vacuum of 30 mm Hg, the reaction is heated to 105° C. for 3.5 hours and generated methanol is removed. The reaction was stopped and the reaction crude was cooled to 100° C. and neutralized with glacial acetic acid. Analysis by gas chromatography indicated that 95% of bis(2,2,6,6-tetramethyl-4-piperidinyl)sebacate is obtained, based on the dimethylsebacate.

The products produced by the process of the present invention are known and can be used as U.V. hindered amine light stabilizers in materials which are subject to degradation, such as plastics, rubbers and other polymers.

Other features, advantages and embodiments of the invention disclosed herein will be readily apparent to those exercising ordinary skill after reading the foregoing disclosures. In this regard, while specific embodiments of the invention have been described in considerable detail, variations and modifications of these embodiments can be effected without departing from the spirit and scope of the invention as described and claimed.

We claim:

1. A process for preparing hindered amine light stabilizers by reacting (a) an alkyl substituted-4-hydroxypiperidine having the following general formula:

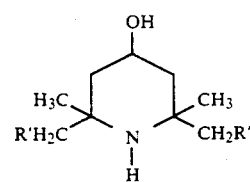

where R' is hydrogen or methyl, with (b) a dicarboxylic acid ester of the formula:

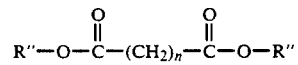

where R'' and R''' are a $C_1$–$C_{12}$ linear or branched alkyl, a $C_5$–$C_{12}$ cycloalkyl, a $C_6$–$C_{12}$ aryl or a $C_7$–$C_{12}$ alkaryl or aralkyl and may be the same or different, and n is a number from 1–12, in the presence of a polar aprotic organic compound and basic inorganic compound catalyst system, wherein a 2:1 to 3.2:1 mole ratio of alkyl substituted-4-hydroxypiperidine to dicarboxylic acid ester is used, and said polar aprotic compound has sufficient polarity to dissolve the ingredients at the reaction temperature and is capable of complexation with the metal ion of said basic inorganic compound.

2. The process according to claim 1, wherein (a) is 2,2,6,6-tetramethyl-4-hydroxypiperidine.

3. The process according to claim 1, wherein (b) is dimethylsebacate.

4. The process according to claim 1, wherein said polar aprotic organic compound is selected from the group consisting of N-methylpyrrolidinone, 1,2-dimethoxybenzene, N,N-dimethylacetamide, hexamethyltriphosphoramide, dimethylaminopyridine, tetramethylenesulfone, tetramethyl glycol dimethylether, ethylene glycol dimethylether, N,N,N',N'-tetramethylethylenediamine, 1,3-dimethyl-2-imidazolidinone, dimethylsulfoxide and 12-crown-4.

5. The process according to claim 4, wherein said polar aprotic organic compound is N-methylpyrrolidinone.

6. The process according to claim 4, wherein said polar aprotic organic compound is 1,2-dimethoxybenzene.

7. The process according to claim 1, wherein said basic inorganic compound is selected from the group consisting of alkali metal hydroxides, alkali metal alkoxides, alkali metal amides, alkali metal alkyl amides and alkali metal hydrides.

8. The process according to claim 7, wherein said basic inorganic compound is selected from the group consisting of potassium methoxide, sodium methoxide, lithium methoxide, potassium ethoxide, sodium ethoxide, lithium ethoxide, potassium-t-butoxide, sodium-t-butoxide, lithium amide, n-butyllithium amide, lithium diisopropyl amide, potassium amide, lithium hydride and sodium hydride.

9. The process according to claim 8, wherein said basic inorganic compound is lithium amide.

10. The process according to claim 1, wherein the reaction temperature is from 80°–165° C.

11. The process according to claim 1 which is conducted under vacuum.

12. The process according to claim 1 which is conducted under a flow of an inert gas at atmospheric pressure.

13. The process according to claim 1 wherein said basic inorganic compound is present in the amount of from 1 to 30 mole % per mole of dicarboxylic acid ester.

14. The process according to claim 1, wherein said basic inorganic compound is present in the amount of 5 to 7 mole % per mole of dicarboxylic acid ester.

15. The process according to claim 1, wherein the ratio of alkyl substituted-4-hydroxypiperidine to dicarboxylic acid ester is 2:1.

16. The process according to claim 1, wherein the ratio of alkyl substituted-4-hydroxypiperidine to dicarboxylic acid ester is 2.6:1.

17. The process according to claim 1, wherein the ratio of alkyl substituted-4-hydroxypiperidine to dicarboxylic acid ester is 3:1.

* * * * *